US007252655B2

(12) United States Patent
Beck et al.

(10) Patent No.: US 7,252,655 B2
(45) Date of Patent: *Aug. 7, 2007

(54) OCULAR IONTOPHORETIC APPARATUS HANDLE

(75) Inventors: Jon E. Beck, Salt Lake City, UT (US); Alex Koss, Salt Lake City, UT (US)

(73) Assignee: Iomed, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/922,559

(22) Filed: Aug. 3, 2001

(65) Prior Publication Data

US 2002/0022794 A1  Feb. 21, 2002

Related U.S. Application Data

(63) Continuation-in-part of application No. 09/599,245, filed on Jun. 22, 2000, now Pat. No. 6,728,573, and a continuation-in-part of application No. 09/318,181, filed on May 25, 1999, now Pat. No. 6,319,240.

(60) Provisional application No. 60/184,498, filed on Feb. 23, 2000.

(51) Int. Cl.
*A61M 35/00* (2006.01)

(52) U.S. Cl. .................. 604/294; 604/20; 604/289; 604/300; 607/115; 607/116; 607/141

(58) Field of Classification Search ............. 604/20, 604/294, 289, 300; 600/372, 373–375, 382, 600/383, 386; 607/113, 115, 116, 98, 99, 607/141

See application file for complete search history.

(56) References Cited

U.S. PATENT DOCUMENTS

| 542,508 | A |   | 7/1895  | Van Tuyl, Jr. |
|---------|---|---|---------|---------------|
| 2,525,381 | A |   | 10/1950 | Tower ................ 128/172.1 |
| 2,635,175 | A | * | 4/1953  | Hodge .................. 607/109 |
| 3,122,137 | A |   | 2/1964  | Erlanger ............. 128/172.1 |
| RE28,873 | E | * | 6/1976  | Morgan .................. 128/249 |
| 4,416,274 | A |   | 11/1983 | Jacobsen et al. ........... 604/20 |
| 4,512,040 | A | * | 4/1985  | McClure ................ 623/6.13 |
| 4,564,016 | A | * | 1/1986  | Maurice et al. ........... 604/20 |

(Continued)

FOREIGN PATENT DOCUMENTS

EP  0927560  7/1999

(Continued)

OTHER PUBLICATIONS

Publication entitled "Investigative Ophthalmology & Visual Science," vol. 31, No. 5, May 1990, pp. 909-916, *Article on Regional Ocular Gentamicin Levels after Transcorneal and Transscleral Iontophoresis*, by Robyn E. Grossman, Douglas F. Chu, and David A. Lee.

(Continued)

*Primary Examiner*—Kevin C. Sirmons
*Assistant Examiner*—Laura C. Schell
(74) *Attorney, Agent, or Firm*—Factor & Lake

(57) ABSTRACT

An iontophoretic apparatus comprising a housing member, a current distribution member, a medicament containment member and at least one of a lateral and medial straddling member. The straddling member are configured to correspond to the surrounding soft tissue.

31 Claims, 3 Drawing Sheets

U.S. PATENT DOCUMENTS

| | | | |
|---|---|---|---|
| 4,678,466 A | 7/1987 | Rosenwald | 604/891 |
| 4,708,716 A | 11/1987 | Sibalis | 604/20 |
| 4,955,378 A | 9/1990 | Grasso | 128/421 |
| 5,053,000 A | 10/1991 | Booth et al. | 604/20 |
| 5,160,316 A | 11/1992 | Henley | 604/20 |
| 5,169,384 A | 12/1992 | Bosniak et al. | 604/20 |
| 5,174,304 A | 12/1992 | Latina et al. | 128/793 |
| 5,370,607 A * | 12/1994 | Memmen | 604/8 |
| 5,472,436 A | 12/1995 | Fremstad | 604/294 |
| 5,720,773 A * | 2/1998 | Lopez-Claros | 607/96 |
| 5,795,342 A * | 8/1998 | Shapiro et al. | 604/300 |
| 6,101,411 A * | 8/2000 | Newsome | 604/20 |
| 6,154,671 A | 11/2000 | Parel et al. | 604/20 |
| 6,319,240 B1 * | 11/2001 | Beck | 604/501 |

FOREIGN PATENT DOCUMENTS

| | | |
|---|---|---|
| FR | 2 585 956 | 8/1985 |
| FR | 98-00009 | 1/1998 |
| GB | 2177928 | 2/1987 |
| JP | 59-113 | 6/1982 |
| JP | 3-70154 | 7/1991 |
| JP | 9-169617 | 12/1995 |
| JP | 11-244323 | 12/1998 |
| RU | 995783 | 7/1980 |
| RU | 942744 | 7/1982 |
| SE | 455375 | 7/1988 |
| SU | 939 019 | 6/1982 |
| SU | 1342500 | 10/1987 |
| WO | WO 89 08474 | 9/1989 |
| WO | WO 90 07954 | 7/1990 |
| WO | WO 96 39095 | 6/1996 |
| WO | WO 97 18855 | 5/1997 |
| WO | WO 99 40967 | 8/1999 |

OTHER PUBLICATIONS

Report entitled *Transscleral Iontophoresis of Gentamicin in Monkeys*, by Michael Barza, Cornelia Peckman, and Jules Branum, No. 6, pp. 1033-1036.

Publication entitled "Journal of Ocular Pharmacology," vol. 10, No. 1, 1994, pp. 69-81, *The Role of Iontophoresis in Ocular Drug Delivery*, by David Sarraf and David A. Lee.

Publication entitled "Ocular Coulomb Controlled Iontophoresis," I. Nose, J-M. Parel, W. Lee, F. Cohen, Y. DeKosac, C. Rowaan, A. Paldano, V. Jallet, P. Soderberg, and J. Davis, referenced in Investigative Ophthalmology & Visual Science, Feb. 15, 1996, vol. 37, No. 3, p. S41.

Publication entitled "Iontophoresis of Dexamethasone in the Treatment of Endotoxin-Induced-Uveitis in Rats," Francine F. Behar-Cohen, Jean-Marie Parel, Yves Pouliquen, Beatrice Thillaye-Goldenberg, Oliver Goureau, Silke Heydolph, Yves Courtois and Yvonne De Kozak, 1997, pp. 533-545.

Frucht-Pery, J., et al, *The Distribution of Gentamicin in the Rabbit Cornea Following Iontophoresis to the Central Cornea*, J. Of Ocular Pharmacology and Therapeutics, vol. 15, No. 3 (1999).

Kiselev, et al, *Procedure for the Administration of Drugs in Gels to Ocular Tissues through the Use of Electrophoresis*, Ministry of Health of the RSFSR publication (1984).

Maurice, D., *Iontophoresis of Fluorescein into the Posterior Segment of the Rabbit Eye*, Opthalmology, vol. 93, No. 1 (Jan. 1986).

Sallmann, L., *Iontophoretic Introduction of Atropine and Scopolamine into the Rabbit Eye*, Archives of Opthalmology, vol. 290, pp. 711-719 (1943).

Barza, M., et al., *Transscleral Iontophoresis of Gentamicin in Monkeys*, Inv. Opthalmology & Vis. Sci., vol. 28, pp. 1033-1036 (Jun. 1987).

Lebedev, O.I., *Electrophoretic Trials in the Early Diagnosis of Primary Glaucoma*, Dissertation by Oleg Ivanovich Lebedev (1983).

Rootman, D., et al, *Iontophoresis of Tobramycin for the Treatment of Experimental Pseudomonas Keratitis in the Rabbit*, Arch. Opthalmology, vol. 106, pp. 262-265 (Feb. 1988).

Rieger, G. et al, *Iodine distribution in a Porcine Eye Model Following Iontophoresis*, Opthalmologica, vol. 209, pp. 84-87 (1995).

* cited by examiner

OCULAR IONTOPHORETIC APPARATUS HANDLE

This application is a continuation-in-part of U.S. Application Ser. No. 09/599,245, filed Jun. 22, 2000, which is now U.S. Pat. No. 6,728,573, which in turn, claims priority from U.S. Provisional Application Ser. No. 60/184,498 filed Feb. 23, 2000. This application is likewise a continuation-in-part of U.S. Application Ser. No. 09/318,181 filed May 25, 1999, which is now U.S. Pat. No. 6,319,240.

BACKGROUND OF THE INVENTION

1. Field of the Invention

The present invention is directed to ocular iontophoretic apparatuses, and more particularly, to a handle for an ocular iontophoretic apparatus (or ocular passive delivery apparatus) to facilitate the grasping, positioning and placement thereof, as well as a retaining member to facilitate the retention thereof in a desired orientation.

2. Background Art

The use of ocular iontophoretic devices has been known in the art. Such devices have been used in an attempt to administer a drug through an electromotive force which drives ionic chemicals through the eye tissue so that they can be absorbed by adjacent tissues and blood vessels.

Among other problems, difficulties can be incurred with the placement of these devices onto the surface of the eye of a patient. Specifically, inasmuch as certain of these devices are intended for use on only a portion of the eye, they are rather small in size. Accordingly, it is difficult for a doctor to carefully position the device in the proper orientation. Moreover, once placed on the patient's eye, it is often difficult to reposition or to adjust the positioning of the device. Further still, it is often difficult to retain the ocular apparatus in the desired orientation for application of medicament.

It will be understood that substantially the same problems and difficulties are associated with passive medicament or fluid delivery devices which are intended for ocular use.

Accordingly, it is an object of the invention to provide for a handle member which facilitates the grasping, positioning and placement of ocular iontophoretic apparatuses (or passive apparatus).

It is a further object of the invention to facilitate the registered maintenance of the ocular apparatus in a desired orientation of the eye.

It is likewise an object of the invention to facilitate the repositioning of an ocular apparatus after placement onto the surface of the eye.

It is a further object of the invention to provide for a handle member which can be pinched so as to flex the iontophoretic apparatus during placement onto an eye and during removal from the eye of the patient.

These and other objects of the invention will become apparent in light of the specification and claims appended hereto.

SUMMARY OF THE INVENTION

The invention comprises an iontophoretic apparatus. The apparatus comprises a housing member, a current distribution member, a medicament containment member and a handle member. The current distribution member is associated with the housing member. The medicament containment member is associated with the current distribution member. The handle member is associated with the housing member. The handle member includes a lateral straddling member and a medial straddling member. The straddling members cooperates with the soft tissue of the eye to retain the apparatus in a desired orientation.

In a preferred embodiment, the handle member comprises a first handle region and a second handle region extending outwardly from the handle member. The first and second handle regions are distally spaced apart a predetermined distance. The lateral straddling member is associated with the first handle region and the medial straddling member is associated with the second handle region.

In another preferred embodiment, at least one of the first and second handle regions includes a gripping region. The gripping region facilitates the grasping of the handle region by a user.

In another preferred embodiment, the straddling members have a width which is such that the opening and closing of an eye is substantially unobstructed.

In another embodiment, at least one of the straddling members includes a width which facilitates retention of an eyelid of a patient in an open position.

Preferably, at least one of the medial and lateral straddling members are substantially flexible so as to facilitate the biasing of the straddling members against respective soft tissue.

In a preferred embodiment, the lateral straddling member is configured to straddle the region encompassed by the lateral angle.

In yet another preferred embodiment, the medial straddling member is configured to straddle the region encompassed by the medial angle, the lacus lacrimalis and the caruncula lacrimalis.

In yet another preferred embodiment, for biasing the straddling members against the soft tissue of an eye.

In another aspect of the invention, the invention comprises an ocular apparatus. The ocular apparatus is similar to the iontophoretic apparatus, however, the delivery of medicament or other fluid is not achieved by way of an electric current, rather, by way of passive delivery. Such an apparatus comprises a housing member, a medicament containment member associated with the housing and at least one of a lateral straddling member and a medial straddling member. The at least one straddling member cooperates with the soft tissue of the eye to retain the apparatus in a desired orientation.

BEST MODE FOR PRACTICING THE INVENTION

Figure 1:
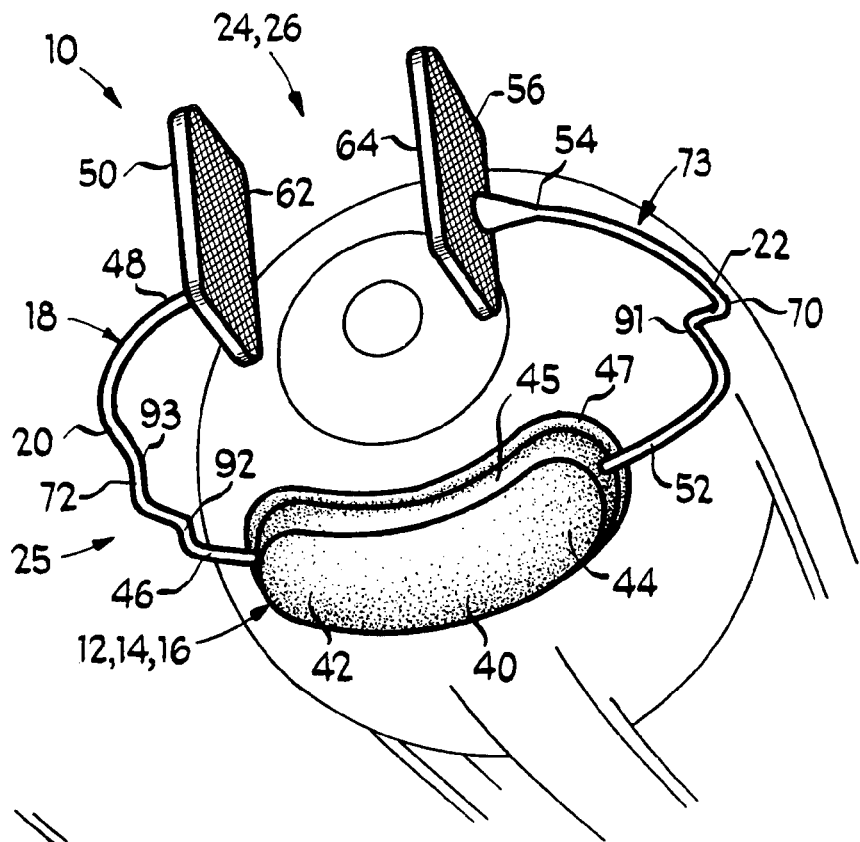
FIG. 1 of the drawings is a perspective view of the apparatus of the present invention showing, in particular, the apparatus placed upon an eye.

While this invention is susceptible of embodiment in many different forms, there is shown in the drawings and will be described in detail, several specific embodiments with the understanding that the present disclosure is to be considered as an exemplification of the principles of the invention and is not intended to limit the invention to the embodiments illustrated.

Figure 2:
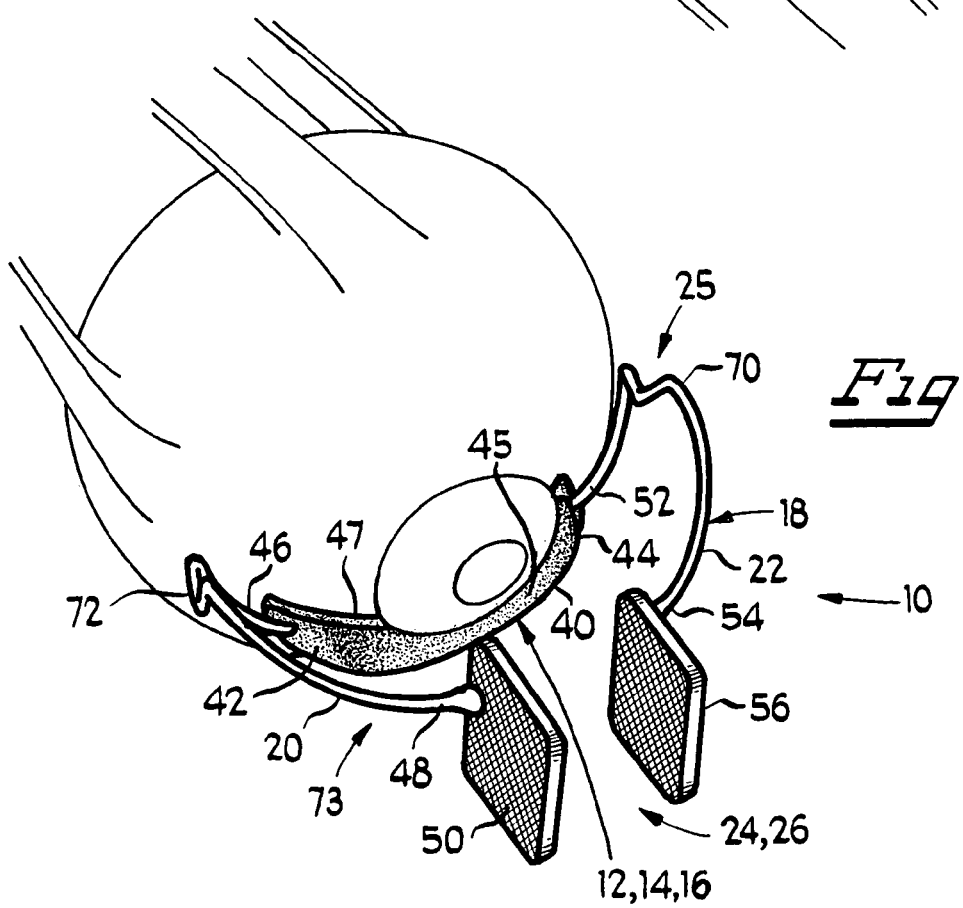
FIG. 2 of the drawings is another perspective view of the apparatus of the present invention showing, in particular, the apparatus placed upon an eye.
Figure 3:
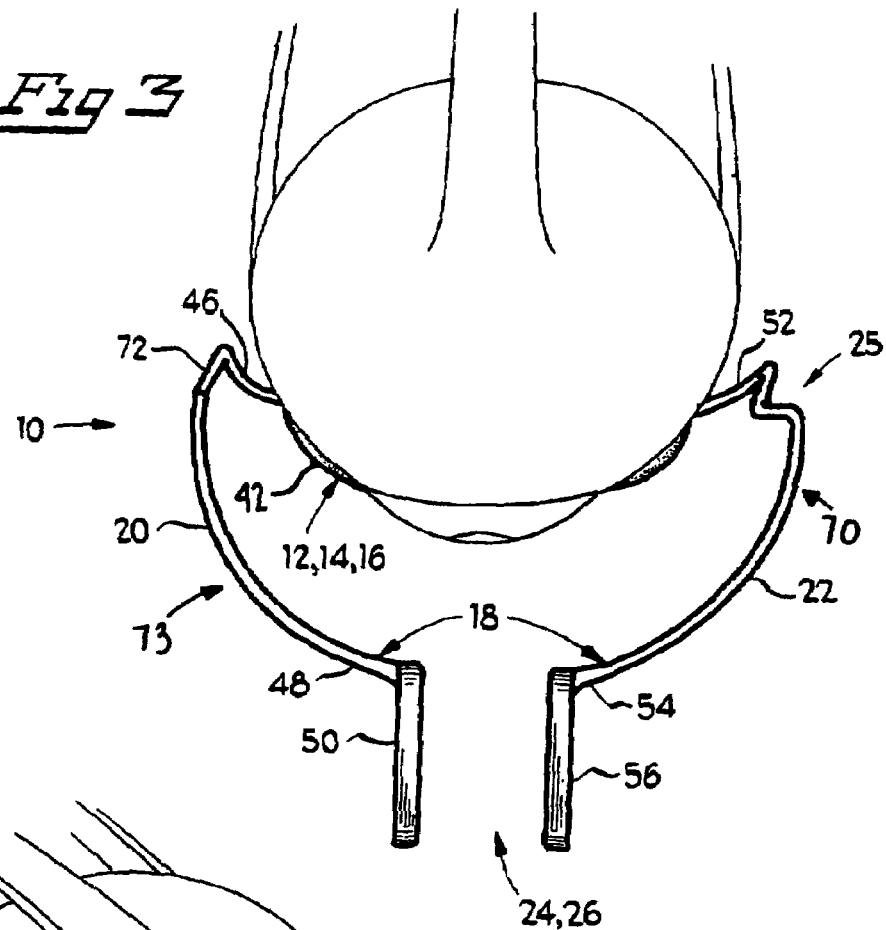
FIG. 3 of the drawings is a top plan view of the apparatus of the present invention showing, in particular, the apparatus placed upon an eye.

Iontophoretic apparatus 10 is shown in FIGS. 1 and 2 as comprising housing member 12, current distribution member 14, medicament containment member 16, handle member 18. The housing member, the current distribution member and the medicament containment member are each described in detail in co-pending application Ser. No. 09/318,181 entitled "Methods and Apparatus for Ocular Iontophoresis," the complete specification of which is incorporated herein by reference. As described therein in greater detail, the housing member includes outer surface 40, first end 42, second end 44, upper region 45 and rim 47. Generally, the housing comprises a plastic material which is molded into a desired configuration for the positioning thereof on the eye of a patient. It will be understood that the medicament containment member can be used to contain medicament, as well as other fluids (lubricating agent, wetting agent, etc.).

It is likewise contemplated that the apparatus may comprise a passive delivery device which includes a housing and a medicament containment member. Such an embodiment has a similar appearance but does not include a current distribution member. As such the medicament is not driven through the surface of the eye; rather, the medicament (or other fluid to be delivered) is permitted to passively be absorbed by the eye. Moreover, it is likewise contemplated that the handle and registration maintaining means described below can be adapted for use in association with other applications to the eye, such as, ERG, Electroretinography, among others.

As will be understood, housing member 12 may be of any number of sizes and shapes. Various embodiments of the housing member may include various configurations depending on the medicament to be dispensed, as well as the specific shape of the soft tissue surrounding the eye of the patient, and the particular region of the eye to which it is to be applied (i.e. under the cornea, above the cornea, in the corners of the eye proximate the medial and lateral angles, etc). Of course, the handle member is not limited to any particular housing member configurations and may be used with a wide variety of such devices. Additionally, the medicament that is retained in medicament containment member 16 for dispensing is not limited to any particular medicament, and virtually any medicament that can be applied iontophoretically through the eye can be used in association with the iontophoretic apparatus.

Figure 4:
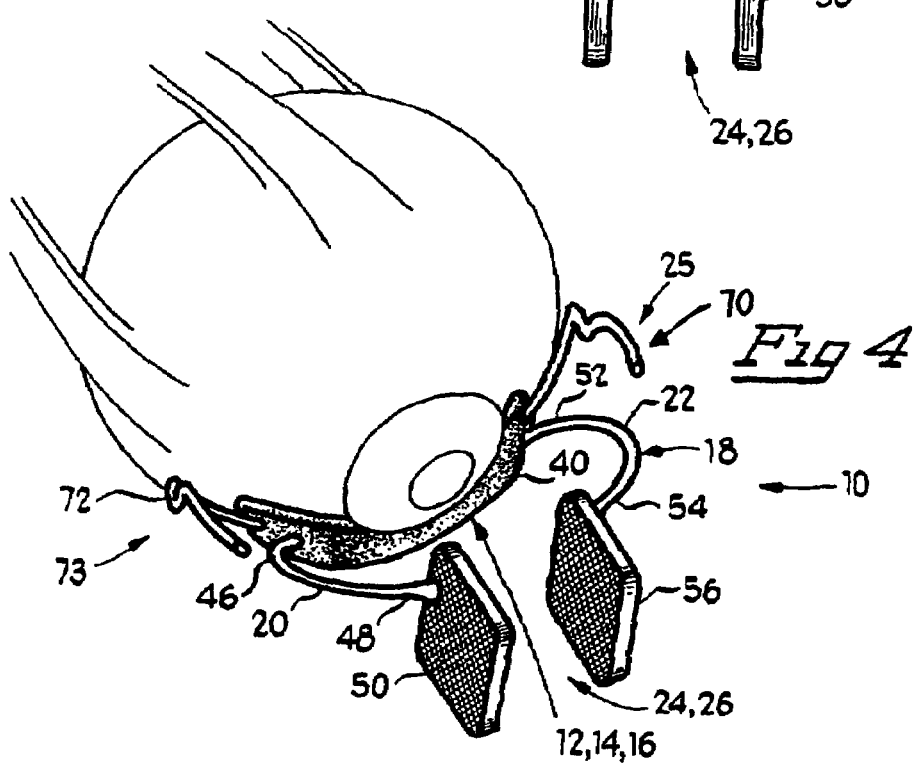
FIG. 4 of the drawings is a front elevational view of an apparatus of the present invention.

Handle member 18 is shown primarily in FIGS. 1 and 2 as comprising first handle region 20, second handle region 22, means 24 for flexing the handle member, means 26 for limiting the flexing of the handle member and means 25 for maintaining registered placement of the apparatus. Generally, handle member 18 is co-molded with housing member 12, however, it is likewise contemplated that the handle member may comprise a separate component which may be welded, adhered or otherwise joined to housing member 12. Of course, as shown in FIG. 4, the registration placement maintaining means 25 can comprise a separate structure which is associated with the housing or with the handle member.

First handle region 20 of the handle member is shown in FIGS. 1 and 2 as including first end 46, second end 48 and first gripping portion 50. First end 46 is associated with outer surface 40 proximate first end 42 of the housing member. Second end 48 extends outwardly therefrom and in a direction which is generally away from second handle region 22 of the handle member. First gripping portion 50 is positioned proximate second end 48 of first handle region 20. Generally, first gripping portion 50 comprises a region which is sized and shaped so as to promote the gripping thereof by a doctor or other professional during placement of the iontophoretic apparatus in the eye of a patient. As can be seen in FIGS. 1 and 2, first gripping portion 50 is spaced apart from the housing member a distance sufficient to insure that the doctor can easily grip the gripping portion without inadvertently striking or touching the patient. It will be understood that second handle region 22 is substantially similar to first handle region 20, and comprises first end 52, second end 54 and second gripping portion 56.

Gripping portion 50 of first handle region 20 and gripping portion 56 of second handle region 22 are spaced apart a predetermined distance from each other, to essentially provide a means for flexing at least one of registration maintaining means 25 and the housing itself. Specifically, and as will be explained in more detail below with respect to the operation, as the doctor or professional pinches the first and second gripping portions 50, 56, about the respective second ends of handle regions 20, 22, toward each other, the force, in turn, flexes the registration maintaining means 25 to facilitate the proper placement of same relative to the soft tissue surrounding the eye that is to receive treatment. Additionally, the housing member may be flexed by the during insertion and positioning on the surface of the eye, so that an improved fit, and an improved positioning can be achieved.

Placement of a gap between the first and second gripping portions defines means 26 for limiting the flexing of the housing member. Specifically, gripping portion 50 and gripping portion 56 extend from the respective second ends of the respective handle regions so as to be substantially parallel to outer surface 40 of housing member 12. The two gripping portions essentially extend toward each other until end 62 of first gripping portion 50 is separated from end 64 of second gripping portion 56 by a gap. Thus, as the user pinches the gripping members, the distance separating the two gripping portions becomes smaller until end 62 of first gripping portion is in abutment with end 64 of second gripping portion 56. At such time, the respective gripping portions can be pinched no further and additional flexing of the registration maintaining means and/or the housing member is not possible. As the respective gripping portions are rather large, it would be difficult to over flex the gripping members as eventual abutment is difficult to avoid.

Placement registration means 25 is shown in FIGS. 1 through 5 as including lateral straddling member 70, medial straddling member 72 and biasing means 73. Lateral straddling member 70 straddles the region encompassed by the lateral angle of the eye. The medial straddling member straddles the region encompassed by at least one of the medial angle, lacus lacrimalis and caruncula lacrimalis.

Figure 5:
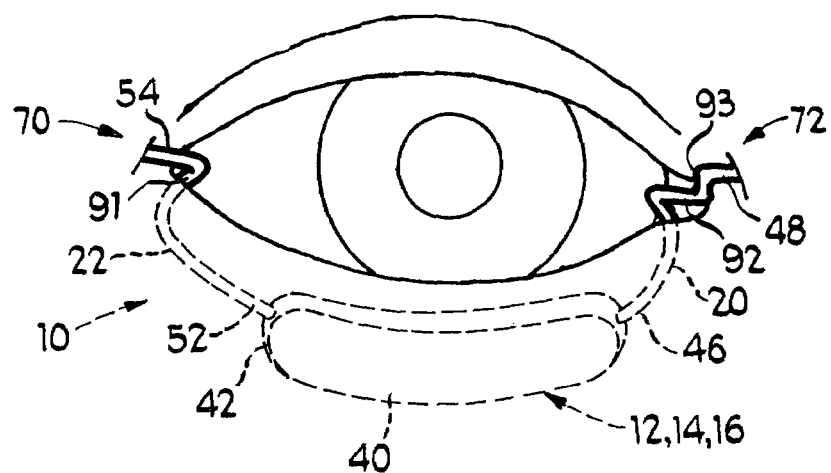
FIG. 5 of the drawings is a front elevational view of an apparatus of the present invention showing, in particular, application thereof within an eye.

Most preferably, and as shown in FIGS. 1 and 5, lateral straddling member includes a single straddling region 91 and medial straddling member includes a first and second straddling region 92, 93, respectively. As such, single straddling region 91 of the lateral straddling member 70 straddles the lateral angle of the eyelid. The first straddling region of the medial straddling member 72 is configured to straddle the medial angle and the second straddling region 93 is configured to straddle at least one of the lacrus lacrimalis and caruncula lacrimalis.

Figure 6:
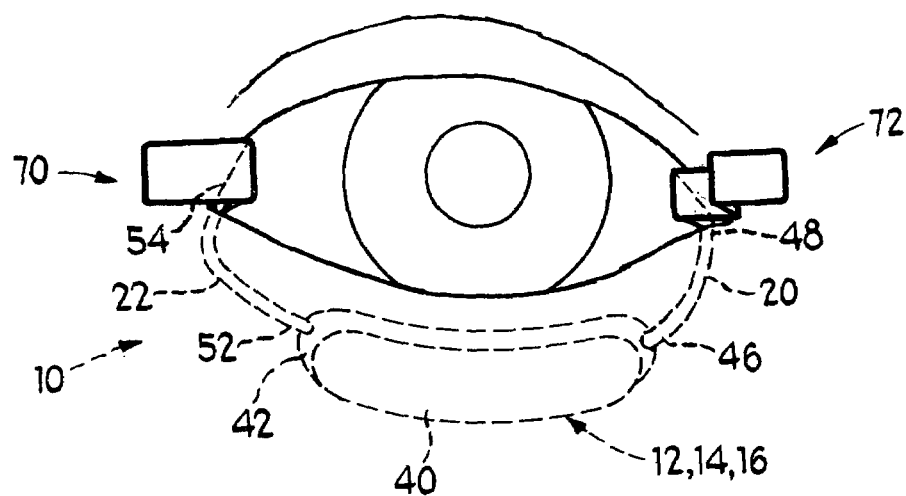
FIG. 6 of the drawings is a front elevational view of an apparatus of the present invention showing, in particular, application thereof within an eye.

In the embodiment shown in FIG. 5, each of the straddling members comprise a narrow wire-like member having a small thickness. Such a narrow member is suitable for receipt proximate the lateral and medial regions such that the patient ability to open and close the eyelid is substantially unaffected. In other embodiments, such as the embodiment shown in FIG. 6, the straddling members may have a larger width which would encompass a wider region around the respective medial and lateral angles. Such an embodiment can spread the force applied by the straddling members along a wider soft tissue surface area and can likewise maintain the eyelids in an open position, if such a maintenance is desirable or necessary.

The configuration of each of the respective straddling members is such that they are spaced apart a distance that is slightly greater than the distance between the medial and lateral angles of the eye. As such, upon application, one of the soft tissue of the eye and the straddling members must be flexed (i.e. manipulated) to achieve the desired registered positioning of the straddling members relative to the eye. Once positioned, the soft tissue is generally biased against the straddling members such that the two are retained in substantial abutment. This cooperation and respective dimensioning of components forms the biasing means 73 referred to in the claims as a means for biasing medial and lateral straddling members against the corner of the eye.

It is contemplated that in certain embodiments, only one of a medial and lateral straddling member can be utilized. For example, a medial straddling member can be utilized proximate the medial angle, and a lateral straddling member can be omitted. Similarly, a lateral straddling member can be utilized proximate the lateral angle, and the medial straddling member can be omitted. Such configurations are useful in association with particularly shaped housings (i.e., housings that are configured to be placed on the eye to cover regions proximate the medial and lateral angle regions).

It is additionally contemplated that the electrical leads which attach the power supply to the electrodes which drive the medicament may be molded into the handle member.

It is contemplated that the registration maintaining means 25 may comprise a structure separate from the handle member or a structure which is not directly a portion of the handle member. Such a structure is shown in FIG. 4, wherein the registration maintaining means 25 include registration regions which cooperate with the soft tissue of the eye. Such an apparatus further includes a separate handle member which is used by the operator to manipulate the apparatus. Such a separate handle member can be associated with either the housing or it may branch from the registration maintaining means. The registration maintaining means 25 can, in such an embodiment, be manipulated independent of the handle members. It is also contemplated that the registration maintaining means 25 can be incorporated with only one of the two handle regions, and omitted with respect to the other of the handle regions.

In operation, the doctor, physician's assistant or other professional first selects the appropriate apparatus from among various apparatuses of different size, shape and medicament. As explained above, the apparatus is not limited to any particular shape and any particular medicament. Once selected and prepared for placement by the doctor or assistant on the patient's eye, the apparatus is grasped by the gripping members and positioned onto the surface of the eye.

In particular, in the embodiment shown in FIG. 1, the doctor first pinches the respective gripping portions 50, 56 toward each other so as to flex registration maintaining means 25 (and to also flex housing member 12 if configured for same). Once the registration maintaining means is flexed as desired, the user can position the housing member on the surface of the patient's eye. As the initial contact with the surface of the eye is attained, the medical professional manipulates the registering regions into the desired configuration relative to the soft tissue surrounding the eye. In particular, the lateral straddling member is positioned to straddle the region encompassed by the lateral angle. Similarly, the medial straddling member is positioned to straddle the region encompassing the medial angle, the lacus lacrimales and the caruncula lacrimales. Each of the straddling regions 91, 92 and 93 are configured to matingly straddle these soft tissue regions.

Furthermore, once fully released, due to the relative spacing between the straddling members, the straddling members are generally biased against the respective soft tissue surrounding the eye due to the biasing means.

Once fully positioned, the doctor initiates current delivery from the current distribution member. The current forces medicament retained in the medicament containment member through the tissue of the patient's eye. The treatment continues for a predetermined period of time which is determined by the type and quantity of medicament that is to be transmitted to the patient.

Once the treatment is complete, current ceases to be delivered by the current distribution member. At such time, passage of medicament through the patient's tissue ceases. When the treatment is complete, the apparatus can be removed from the patient. Specifically, the doctor again grasps the gripping regions of handle member 12 and pulls the housing from the surface of the eye.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. An ocular apparatus for medically treating an eye, the ocular apparatus being capable of cooperating with soft tissue proximate the eye, the ocular apparatus comprising:
   a medicament containment member;
   a handle is affixed to the medicament containment member;
   a registration member attached to the medicament containment member and extending outwardly there from, wherein placement of the medicament containment member directly on the eye is maintained by operable cooperation of the registration member and soft tissue proximate the eye;
   a means for biasing the abutment of the registration member with the soft tissue proximate the eye; and,
   a current distribution member in electrical communication with the medicament containment member.

2. The ocular apparatus of claim 1 wherein maintaining the placement of the medicament containment member directly on the eye is facilitated by the abutment of the registration member proximate soft tissue of the eye.

3. The ocular apparatus of claim 1 wherein the registration member includes a width such that opening and closing of the eye is substantially unobstructed.

4. The ocular apparatus of claim 1 wherein the registration member includes a width to retain an eyelid in an open position.

5. The ocular apparatus of claim 1 wherein the registration member further comprising:
a lateral member including a first end and a second end, the first end of the lateral member being affixed to the medicament containment member and extending outwardly there from; and,
a medial member including a first end and a second end, the first end of the medial member being affixed to the medicament containment member and extending outwardly there from.

6. The ocular apparatus of claim 5 wherein at least one of the lateral and medial members of the registration member includes a width such that opening and closing of the eye is substantially unobstructed.

7. The ocular apparatus of claim 5 wherein at least one of the lateral and medial members of the registration member includes a width to retain an eyelid in an open position.

8. The ocular apparatus of claim 1 wherein the means for biasing simultaneously maintains the abutment of the lateral member with lateral soft tissue proximate the eye and the abutment of the medial member with medial soft tissue proximate the eye.

9. The ocular apparatus of claim 1 the handle member further comprising:
a first member including a first end and a second end, the first end of the first member being affixed to the medicament containment member; and,
a second member including a first end and a second end, and the first end of the second member being affixed to the medicament containment member.

10. The ocular apparatus of claim 9 further comprising:
a first grip portion attached to the second end of the first member of the handle; and,
a second grip portion attached to the second end of the second member of the handle, wherein the first and second grip portions facilitate grasping of the handle.

11. The ocular apparatus of claim 1 wherein the handle includes a wire.

12. The ocular apparatus of claim 1 wherein the registration member includes a wire.

13. The ocular apparatus of claim 1 wherein the handle is unitarily configured with the medicament containment member and extends therefrom.

14. The ocular apparatus of claim 1 wherein the registration member is unitarily configured with the medicament containment member and extends therefrom.

15. The ocular apparatus of claim 1 wherein the handle is connected to the registration member.

16. An ocular apparatus for medically treating an eye, the ocular apparatus being capable of cooperating with soft tissue proximate the eye, the ocular apparatus comprising:
a medicament containment member;
a handle operably connected to the medicament containment member, the handle including a lateral straddling member and a medial straddling member, the lateral straddling member including a first end and a second end, the medial straddling member including a first end and a second end, the first end of the lateral straddling member connected to the medicament containment member and the first end of the medial straddling member connected to the medicament containment member, wherein placement of the medicament containment member directly on the eye is maintained by the operable cooperation of the handle and soft tissue proximate the eye;
a means for biasing the abutment of the handle with soft tissue proximate the eye; and,
a current distribution member in electrical communication with the medicament containment member.

17. The ocular apparatus of claim 16 wherein maintaining placement of the medicament containment member directly on the eye is facilitated by the abutment of lateral straddling member proximate lateral soft tissue of the eye and the abutment of the medial straddling member proximate medial soft tissue of the eye.

18. The ocular apparatus of claim 17 wherein the medial and lateral straddling members each include a width such that opening and closing of the eye is substantially unobstructed.

19. The ocular apparatus of claim 16 further comprising:
a first grip portion attached to the second end of the lateral straddling member; and,
a second grip portion attached to the second end of the medial straddling member wherein the first and second grip portions facilitate grasping of the handle.

20. The ocular apparatus of claim 16 wherein at least one of the lateral or medial straddling members includes a width to retain an eyelid in an open position.

21. The ocular apparatus of claim 16 wherein the means for biasing simultaneously maintains the abutment of the lateral straddling member with lateral soft tissue proximate the eye and the abutment of the medial straddling member with medial soft tissue proximate the eye.

22. The ocular apparatus of claim 16 wherein the handle includes a wire.

23. The ocular apparatus of claim 16 wherein the handle is unitarily configured with the medicament containment member and extends therefrom.

24. An ocular apparatus for medically treating an eye, the ocular apparatus being capable of cooperating with soft tissue proximate the eye, the ocular apparatus comprising:
a medicament containment member;
a handle operably connected to the medicament containment member, the handle including a lateral straddling member and a medial straddling member, the lateral straddling member including a first end and a second end, the medial straddling member including a first end and a second end, the first end of the lateral straddling member connected to the medicament containment member and the first end of the medial straddling member connected to the medicament containment member, wherein placement of the medicament containment member directly on the eye is maintained by the operable cooperation of the handle and soft tissue proximate the eye;
a first grip portion attached to the second end of the lateral straddling member;
a second grip portion attached to the second end of the medial straddling member wherein the first and second grip portions facilitate grasping of the handle; and,
a current distribution member in electrical communication with the medicament containment member.

25. The ocular apparatus of claim 24 wherein maintaining placement of the medicament containment member directly on the eye is facilitated by the abutment of lateral straddling member proximate lateral soft tissue of the eye and the medial straddling member proximate medial soft tissue of the eye.

26. The ocular apparatus of claim 25 wherein the medial and lateral straddling members each include a width such that opening and closing of the eye is substantially unobstructed.

27. The ocular apparatus of claim 24 wherein at least one of the lateral or medial straddling members includes a width to retain an eyelid in an open position.

28. The ocular apparatus of claim 24 further comprising:
a means for biasing the abutment of the handle with soft tissue proximate the eye.

29. The ocular apparatus of claim 28 wherein the means for biasing simultaneously maintains the abutment of the lateral straddling member with lateral soft tissue proximate the eye and the abutment of the medial straddling member with medial soft tissue proximate the eye.

30. The ocular apparatus of claim 24 wherein the handle includes a wire.

31. The ocular apparatus of claim 24 wherein the handle is unitarily configured with the medicament containment member and extending there from.

* * * * *